United States Patent
Meir et al.

(10) Patent No.: US 12,042,671 B2
(45) Date of Patent: Jul. 23, 2024

(54) METHOD OF CALIBRATION OF A STEREOSCOPIC CAMERA SYSTEM FOR USE WITH A RADIO THERAPY TREATMENT APPARATUS

(71) Applicant: Vision RT Limited, London (GB)

(72) Inventors: Ivan Meir, London (GB); Martin Allen, London (GB); Gideon Hale, London (GB); Norman Smith, London (GB); Robert Howe, London (GB)

(73) Assignee: VISION RT LIMITED, London (GB)

( * ) Notice: Subject to any disclaimer, the term of this patent is extended or adjusted under 35 U.S.C. 154(b) by 0 days.

(21) Appl. No.: 18/542,832

(22) Filed: Dec. 18, 2023

(65) Prior Publication Data

US 2024/0123260 A1    Apr. 18, 2024

Related U.S. Application Data

(60) Division of application No. 18/487,148, filed on Oct. 16, 2023, which is a continuation of application No.
(Continued)

(30) Foreign Application Priority Data

Jul. 17, 2013    (GB) ...................................... 1312808

(51) Int. Cl.
*A61N 5/10*    (2006.01)
*A61B 6/58*    (2024.01)
(Continued)

(52) U.S. Cl.
CPC ............ *A61N 5/1075* (2013.01); *A61B 6/584* (2013.01); *A61N 5/1049* (2013.01);
(Continued)

(58) Field of Classification Search
None
See application file for complete search history.

(56) References Cited

U.S. PATENT DOCUMENTS

| | | | | |
|---|---|---|---|---|
| 5,859,922 A | * | 1/1999 | Hoffmann | ................. G06T 7/74 |
| | | | | 382/128 |
| 6,345,114 B1 | * | 2/2002 | Mackie | ................. A61N 5/1048 |
| | | | | 378/65 |

(Continued)

FOREIGN PATENT DOCUMENTS

WO    WO-2010065740 A2 *    6/2010    ........... A61N 5/1075

OTHER PUBLICATIONS

Apr. 28, 2018 Second Office Action issued in corresponding Chinese Patent Application No. 201480040129.3 (with English Translation).
(Continued)

*Primary Examiner* — Reza Aghevli

(57) ABSTRACT

The disclosed calibration method includes a calibration phantom positioned on an adjustable table on the surface of a mechanical couch, with the phantom's centre at an estimated location for the iso-centre of a radio therapy treatment apparatus. The calibration phantom is then irradiated using the apparatus, and the relative location of the center of the calibration phantom and the iso-centre of the apparatus is determined by analyzing images of the irradiation of the calibration phantom. The calibration phantom is then repositioned by the mechanical couch applying an offset corresponding to the determined relative location of the centre of the calibration phantom and the iso-centre of the apparatus to the calibration phantom. Images of the relocated calibration phantom are obtained, to which the offset has been applied, and the obtained images are processed to set the
(Continued)

co-ordinate system of a stereoscopic camera system relative to the iso-centre of the apparatus.

13 Claims, 2 Drawing Sheets

Related U.S. Application Data

18/124,273, filed on Mar. 21, 2023, which is a continuation of application No. 17/159,845, filed on Jan. 27, 2021, now Pat. No. 11,633,629, which is a continuation of application No. 16/578,905, filed on Sep. 23, 2019, now Pat. No. 10,933,258, which is a continuation of application No. 15/946,362, filed on Apr. 5, 2018, now Pat. No. 10,456,601, which is a continuation of application No. 14/899,112, filed as application No. PCT/GB2014/052125 on Jul. 11, 2014, now Pat. No. 9,962,561.

(51) Int. Cl.
  *G06T 7/00* (2017.01)
  *G06T 7/80* (2017.01)
(52) U.S. Cl.
  CPC .............. *G06T 7/0012* (2013.01); *G06T 7/85* (2017.01); *A61N 2005/1059* (2013.01); *A61N 2005/1076* (2013.01); *G06T 2207/30004* (2013.01)

(56) References Cited

U.S. PATENT DOCUMENTS

| | | | | |
|---|---|---|---|---|
| 6,484,049 B1* | 11/2002 | Seeley | .................. | A61B 90/36 |
| | | | | 600/431 |
| 6,990,228 B1* | 1/2006 | Wiles | ..................... | G06T 7/55 |
| | | | | 348/42 |
| 7,345,274 B2* | 3/2008 | Nilsson | ................ | A61N 5/1048 |
| | | | | 378/207 |
| 7,348,974 B2* | 3/2008 | Smith | ..................... | G06T 7/80 |
| | | | | 378/57 |
| 7,843,429 B2* | 11/2010 | Pryor | ................... | G06V 40/20 |
| | | | | 345/158 |
| 7,889,906 B2* | 2/2011 | Smith | ................. | A61N 5/1049 |
| | | | | 382/294 |
| 8,068,646 B2* | 11/2011 | Fenrich | ............. | G06V 40/1347 |
| | | | | 382/124 |
| 8,135,201 B2* | 3/2012 | Smith | ..................... | G06T 7/75 |
| | | | | 703/2 |
| 8,441,476 B2* | 5/2013 | Gloudemans | ............. | G06T 5/77 |
| | | | | 345/650 |
| 8,602,647 B2* | 12/2013 | Navarro | .................. | G01T 1/185 |
| | | | | 378/65 |
| 9,731,150 B2* | 8/2017 | Hale | .................... | A61B 5/0071 |
| 9,962,561 B2* | 5/2018 | Meir | ................... | A61N 5/1075 |
| 10,456,601 B2* | 10/2019 | Meir | ..................... | A61N 5/1075 |
| 10,933,258 B2* | 3/2021 | Meir | ..................... | A61N 5/1075 |
| 11,600,004 B2* | 3/2023 | Kapatoes | ............... | A61N 5/103 |
| 11,794,037 B2* | 10/2023 | Ramezanzadeh Moghadam | ........ | |
| | | | | G16H 20/40 |
| 2002/0080912 A1* | 6/2002 | Mackie | ................. | A61N 5/1048 |
| | | | | 398/182 |
| 2003/0066949 A1* | 4/2003 | Mueller | ............... | H04N 13/254 |
| | | | | 348/E13.016 |
| 2003/0068949 A1 | 7/2003 | Mueller et al. | | |
| 2003/0130576 A1* | 7/2003 | Seeley | ................... | A61B 90/36 |
| | | | | 600/426 |
| 2005/0089213 A1* | 4/2005 | Geng | ......................... | G06T 7/33 |
| | | | | 382/154 |
| 2006/0259282 A1* | 11/2006 | Failla | ..................... | G06T 15/06 |
| | | | | 703/2 |
| 2007/0076946 A1* | 4/2007 | Kunisaki | .............. | G01B 21/042 |
| | | | | 382/153 |
| 2007/0132763 A1* | 6/2007 | Chu | ....................... | G06T 11/203 |
| | | | | 345/442 |
| 2008/0069445 A1* | 3/2008 | Weber | ..................... | G06T 7/149 |
| | | | | 382/181 |
| 2009/0187112 A1 | 7/2009 | Meir et al. | | |
| 2009/0207246 A1* | 8/2009 | Inami | ..................... | H04N 7/181 |
| | | | | 348/E7.086 |
| 2010/0028891 A1 | 2/2010 | Cho | | |
| 2010/0288916 A1* | 11/2010 | Cho | ........................ | G01D 15/00 |
| | | | | 378/207 |
| 2011/0222737 A1* | 9/2011 | Biskup | ..................... | G06T 7/62 |
| | | | | 382/110 |
| 2011/0278444 A1* | 11/2011 | Navarro | .................. | G01T 1/169 |
| | | | | 250/252.1 |
| 2011/0305380 A1* | 12/2011 | Bose | ..................... | A61N 5/1075 |
| | | | | 382/132 |
| 2012/0259204 A1* | 10/2012 | Carrat | .................... | A61B 34/20 |
| | | | | 600/414 |
| 2012/0305793 A1* | 12/2012 | Schiefer | ............... | A61N 5/1048 |
| | | | | 250/394 |
| 2014/0104395 A1* | 4/2014 | Rohaly | ................ | G01B 11/245 |
| | | | | 348/47 |
| 2014/0369584 A1* | 12/2014 | Fan | ....................... | G06T 7/0012 |
| | | | | 382/131 |
| 2015/0094564 A1* | 4/2015 | Tashman | ................. | A61B 6/563 |
| | | | | 600/407 |
| 2016/0129283 A1* | 5/2016 | Meir | ...................... | A61B 6/584 |
| | | | | 348/46 |
| 2016/0332000 A1* | 11/2016 | Hale | ......................... | G01T 1/29 |
| 2017/0319874 A1* | 11/2017 | Mead | ................... | H04N 13/204 |
| 2018/0252790 A1* | 9/2018 | Vesanen | ............... | G01R 33/543 |
| 2019/0255358 A1* | 8/2019 | Hale | ..................... | A61N 5/1049 |

OTHER PUBLICATIONS

Arp et al., "Exactrac x-ray and beam isocenters—What's the difference?," Medical Physics 39 (3), Mar. 2012, pp. 1418-1423. (Year 2012).
Daniel A. Low, et al., "Minimization of target positioning error in accelerator-based radiosurgery"; Medical physics; Apr. 1995, 22(4); pp. 443-448.
Dec. 7, 2017 Communication pursuant to Rule 1654(2)(b) and Article 94(3) EPC issued in corresponding European Patent Applicaiton No. 14 739 544.6-1666.
E-Beam Services, "Relative Radiation Stability of Medical Polymers," 2012, p. 1. (Year 2012).
Eduard Schreibmann, et al., "Automated Quality Assurance for Image-Guided Radiation Therapy", Journal of Applied Clinical Medical Physics, 2009:10(1); pp. 71-79.
Grelewicz Zachary et al.: "An EPID bsed method for performing high accuracy calibration between an optical external marker tracking device and the LINAC reference frame", Medical Physics, AIP, Melville, NY, US, vol. 39. No. 5, May 1, 2012 (May 1, 2012), pp. 2771-2779.
International Search Report and the Written Opinion of the International Searching Authority issued in International Applicaiton No. PCT/GB2014/052125.
Invitation to Pay Additional Fees with partial Search Report issued in International Application No. PCT/GB2014/052125.
Jimm Grimm, et al., "A quality assurance method with submillimeter accuracy for stereotactic linear accelerators"; Journal of Applied Clinical Medical Physics, vol. 12, No. 1; pp. 182-198.
Nov. 30, 2017 Office Action issued in corresponding Chinese Patent Application No. 201480040129.3 (with English Translation).
Roger Tsai, "A Versatile Camera Calibration Technique for High-Accuracy 3D Machine Vision Metrology Using Off the Shelf TV Cameras and Lenses"; IEEE Journal of Robotics & Automation, vol. Ra-3, No. 4, Aug. 1987.
Search Report under Section 17 (5) issued in GB Application No. GB1312808.7.
Wendell Lutz, et al., "A System for Stereotactic Radiosurgery With a Lin era Accelerator": International Journal of Radiation Oncology Biology Physics (Impact Factor: 4.26). Mar. 1988; 14(2); pp. 373-381.

(56) References Cited

OTHER PUBLICATIONS

Wiski, "Radiation stability of polymers," International Journal of Radiation Applications and Instrumentation, Part C, Radiation Physics and Chemistry, col. 35, issues 1-3, 1990, Abstract. (Year: 1990).

* cited by examiner

METHOD OF CALIBRATION OF A STEREOSCOPIC CAMERA SYSTEM FOR USE WITH A RADIO THERAPY TREATMENT APPARATUS

CROSS REFERENCE TO RELATED APPLICATIONS

Any and all application for which a foreign or domestic priority claim is identified in the Application Data Sheet as filed with the present application are hereby incorporated by reference under 37 CFR 1.57.

BACKGROUND

The present invention concerns a method of calibration of a stereoscopic camera system. In particular, embodiments of the present invention concern a method of calibration of a stereoscopic camera system for use with a radio therapy treatment apparatus.

Radiotherapy consists of projecting, onto a predetermined region of a patient's body, a radiation beam so as to destroy or eliminate tumours existing therein. Such treatment is usually carried out periodically and repeatedly. At each medical intervention, the radiation source must be positioned with respect to the patient in order to irradiate the selected region with the highest possible accuracy to avoid radiating adjacent tissue on which radiation beams would be harmful.

A fundamental problem with radiotherapy is the need to position the patient in the same position, when obtaining diagnostic images and each of the subsequent times when radiation is applied to the patient's body. It is to that end that Vision RT have developed an image processing system for monitoring and positioning patients described in U.S. Pat. Nos. 7,348,974, 7,889,906, 8,135,201, and pending U.S. patent application Ser. No. 12/379,108, published as U.S. 2009/0187112.

In use, in the Vision RT system, images of a patient on a mechanical couch are obtained by a set of stereoscopic cameras which are then processed to generate a 3D wire mesh model of the surface of a patient being monitored. This 3D wire mesh model is compared with a reference surface created during treatment planning The relative positioning of the model and the reference surface is compared and used to generate instructions for the mechanical couch to position the couch, vertically, laterally and rotationally so as to match the surfaces and hence locate the patient reliably in the same location relative to the iso-centre of a treatment apparatus. Subsequently during treatment, the position of a patient is continually monitored and if for any reason the patient moves or repositions themselves, this can be detected and appropriate action can be taken if necessary.

There are several sources of uncertainty in radio therapy treatment systems such as errors in patient positioning, target localization, and dose delivery. It is practically impossible to achieve perfect alignment mainly due to the presence of several geometric errors in the system. One of the critical geometric errors in radio therapy treatments is uncertainty in localizing the radiation field centre, which directly affects the dosimetric accuracy and results in incorrect tumour targeting that may lead to the delivery of inadequate dose to the lesion and/or serious damage to the healthy adjacent tissues. Therefore, it is necessary to develop methods to reduce the probability of such errors by extensive and efficient quality assurance programs to ensure high-level geometric accuracy of the treatment.

Originally, the primary method for iso-centre verification in radiotherapy was to measure the distance between the tip of a mechanical pointer mounted on the gantry head of a treatment apparatus and a fixed point mounted on the treatment table. Such a method was manual, laborious and time-consuming. The accuracy of the method depended upon the human observer and was also limited by size of the tip of pointer used.

An improved technique was introduced by Lutz, Winston and Maleki at Harvard Medical School in 1988 which is described in Lutz W, Winston K R, Maleki N. A system for stereotactic radiosurgery with a linear accelerator. Int J Radiat Oncol Biol Phys. 1988; 14(2):373 -81. In the Winston-Lutz system a calibration phantom comprising a small metallic ball made of steel, titanium or tungsten is fixed on the treatment table by a locking mechanism. The phantom position is adjustable in three directions by means of a micrometer tool. The collimator used for radiotherapy is attached to the gantry head and the ball is placed as closely as possible to the iso-centre by aligning the marks on the phantom with the treatment room lasers. The collimated beam is used to expose a radiographic test film mounted perpendicular to the beam direction on a stand behind the ball. Differences between the centre of the sphere shadow and the field centre identifies the differences between the true iso-centre and the iso-centre as indicated by the treatment room lasers. The offset is read on each film using transparent template guidance scales or scanning the film and software analysis.

A mathematical method for analysing Winston Lutz images was developed and is described in Low D A, Li Z, Drzymala R E. Minimization of target positioning error in accelerator-based radiosurgery. Med Phys. 1995; 22(4):443-48 which used the film-measured iso-centre positional errors for eight gantry angle and couch settings to find the suitable offset for the phantom stand to minimize the distance between the treatment apparatus iso-centre and the target. A similar aim was followed by Grimm et al., who developed an algorithm to reconstruct the Winston-Lutz phantom ball locus in three dimensions from two-dimensional film images taken at certain couch and gantry angles and combined them with the images of lasers taken by digital cameras. This approach is described in Grimm J, Grimm S L, Das I J, et al. A quality assurance method with sub-millimetre accuracy for stereotactic linear accelerators. J Appl Clin Med Phys. 2011; 12(1):182-98.

A further example of automated processing of phantom images is described in E Schriebmann, E Elder and T Fox, Automatied Quality Assurance for Image-Guided Radiation Therapy, J Appl Clin Med Phys. 2009:10(1):71-79 which discusses the automation of Quality Assurance methods to ensure that a megavoltage (MV) treatment beam coincides with an integrated kilovoltage (kV) or volumetric cone beam CT. In the paper, a calibration cube is described as being located at the estimated location of treatment room iso-centre using laser markings. Images of the irradiation of the cube are then obtained and processed to determine the extent the cube as positioned is offset from the iso-centre as identified by the MV, kV and volumetric cone beams.

Calibration of stereoscopic camera systems for use in treatment rooms has developed alongside methods for identifying the iso-centre of a treatment apparatus. Calibration techniques used to calibrate the Vision RT patient monitoring system are described in U.S. Pat. Nos. 7,348,974 and 7,889,906.

As is described in U.S. Pat. Nos. 7,348,974 and 7,889,906 a calibration sheet comprising a 40*40 cm sheet of flat rigid material such as aluminium or steel on which a pattern revealing a 20*20 matrix of circles at known positions on the surface of the sheet is provided. Additionally, towards the centre of the calibration sheet are four smaller markers adjacent to four circles the centres of which together identify the four corners of a square of known size.

Images of the calibration sheet are obtained and processed to identify within the image the positions of the four markers in the images and their associated circles. From the relative positions of circles identified by the markers in the images, a projective transformation is determined which accounts for the estimated centres of the identified circles defining the corners of a parallelogram in the image which arises due to the relative orientation of the calibration sheet and the camera obtaining the image. The calculated transform is then applied to each of the identified circles in turn to transform the oval shapes of the circles. More accurate estimates of the positions of the centres of the four circles are then determined by identifying the centres of the transformed circles and utilising an inverse transform to determine the corresponding position of the estimated circle centre in the original image.

When the co-ordinates for all the centres of each of the representations of the circles on the calibration sheet have been calculated for an image, the relative orientation of the different cameras can then be calculated from the relative positions of these points in the images and the known relative locations of these circles on the surface of the calibration sheet as is described in detail in "A Versatile Camera Calibration Technique for High-Accuracy 3D Machine Vision Metrology Using Off the Shelf TV Cameras and Lenses", Roger Tsai, IEEE Journal of Robotics and Automation, Vol. Ra-3, No. 4, August 1987. Further from the relative positions of the points in the individual images internal camera parameters such as the focal length and radial distortion within the camera images can also be determined.

Having determined the locations of the stereoscopic cameras, and any radial distortions present in the camera images, the positioning of the cameras relative to the iso-centre of the treatment apparatus is then determined. This is achieved by imaging a calibration cube of known size which is positioned on a treatment apparatus at a position with its centre at the iso-centre of the treatment apparatus as indicated by the co-incidence of marks on the exterior of the cube with the projection of the laser cross hairs which intersect at the iso-centre.

The images of the calibration cube are processed utilising the previously obtained measurements of the relative locations of the cameras and any data about the existence of any distortion present in the images to generate a 3D computer model of the surface of the cube. Since the cube has known dimensions and is at a known location and in a known orientation relative to the iso-centre of the treatment apparatus as indicated by the laser cross-hairs, a comparison between the generated 3D model and the known parameters for the size and position of the calibration cube enables measurements made in the co-ordinate system of the modelling software to be converted into real world measurements in the treatment room relative to the treatment iso-centre.

Although the conventional approach to calibrating a stereoscopic camera system for use with a radio therapy treatment apparatus is highly accurate, further improvements in accuracy are desirable.

SUMMARY

In accordance with one aspect of the present invention there is provided a method of calibration of a stereoscopic camera system for use with a radio therapy treatment apparatus.

In the method, initially a calibration phantom is positioned with the phantom's centre at an estimated location for the iso-centre of a radio therapy treatment apparatus. The calibration phantom is then irradiated using the radio therapy treatment apparatus. The relative location of the centre of the calibration phantom and the iso-centre of the radio therapy treatment is then determined by analysing images of the irradiation of the calibration phantom. The calibration phantom is then repositioned, applying an offset corresponding to the determined relative location of the centre of the calibration phantom and the iso-centre of the radio therapy treatment apparatus to the calibration phantom. The stereoscopic camera system then proceeds to obtain images of the relocated calibration phantom to which the offset has been applied, processing the images to set the co-ordinate system of the stereoscopic camera system relative to the iso-centre of the radio therapy treatment apparatus.

Thus in this way the co-ordinate system for the stereoscopic camera system is established based directly on the positioning of a calibration phantom where the calibration phantom's location is directly linked to a determination of the iso-centre of a treatment apparatus.

In some embodiments, the stereoscopic camera system may additionally be utilised to monitor the repositioning of the calibration phantom. This may involve processing images of a relocated calibration phantom and comparing a generated 3D computer model of the surface of the repositioned calibration phantom with a 3D computer model of the expected surface of the calibration phantom positioned at the iso-centre of the treatment apparatus.

In such embodiments the 3D computer model of the expected surface of the calibration phantom positioned at the iso-centre of the treatment apparatus may comprise a stored 3D computer model of the surface of the calibration phantom.

Alternatively, the stereoscopic camera system may be utilised to generate a 3D computer model of the expected surface of the calibration phantom positioned at the iso-centre of the treatment apparatus. In such a system initially a model of the surface of the phantom may be generated by processing images of the calibration phantom positioned at the estimated location for the iso-centre of the radio therapy treatment apparatus. A model of the expected surface of the calibration phantom may then be generated by applying an offset corresponding to the determined relative location of the centre of the calibration phantom and the iso-centre of the radio therapy treatment apparatus to the generated model.

In some embodiments, a calibration phantom may be positioned at the estimated location of the iso-centre of a treatment apparatus by being placed on a mechanical couch. In such embodiment, relocating the calibration phantom may be achieved by instructing the mechanical couch to offset the current location of the calibration phantom by an offset corresponding to the determined relative location of the centre of the calibration phantom and the iso-centre of the radio therapy treatment apparatus.

In some embodiments an adjustable table may be used to level a calibration phantom. The adjustable table may be placed on the surface of a mechanical couch. In such embodiments the calibration phantom may be fixed on the adjustable table with the adjustable table being levelled thereby levelling the calibration phantom. In such embodiments the adjustable table may include a spirit level to facilitate levelling a calibration phantom by adjusting the adjustable table.

In embodiments of the claimed invention a calibration phantom may comprise a calibration phantom containing one or more calibration targets. In embodiments where the calibration phantom contains multiple calibration targets, preferably the calibration targets are arranged asymmetrically within the calibration phantom so assist with the analysis of images of an irradiated phantom.

Analysing images of the irradiation of the calibration phantom may comprise determining the relative location of the centre of the calibration phantom and the iso-centre of the radio therapy treatment apparatus by comparing the locations of the one or more targets in images of the irradiated calibration phantom irradiated with the treatment apparatus being in a number of different positions.

In some embodiments the relocation of a calibration phantom may be undertaken iteratively. That is to say that having relocated a calibration phantom, the relocated calibration phantom may be irradiated and imaged whilst in its new location. The relative location of the centre of the relocated calibration phantom and the iso-centre of the radio therapy treatment apparatus can then be determined by analysing images of the irradiation of the relocated calibration phantom. The calibration phantom may then be further relocated by applying an offset corresponding to the determined relative location of the centre of the relocated calibration phantom and the iso-centre of the radio therapy treatment apparatus to the relocated calibration phantom. The co-ordinate system of the stereoscopic camera system may then be set by processing obtained images of the calibration phantom as relocated.

In some embodiments multiple calibration phantoms may be used. More specifically, an initial estimate of the location of the iso-centre of a treatment apparatus may be obtained by irradiating a first calibration phantom and positioning the calibration phantom on the basis of analysis of images of the irradiated calibration phantom. The first calibration phantom could then be replaced and further adjustments of position may be determined utilising that second calibration phantom.

In such systems initially a first phantom containing multiple calibration targets could be used. Where such targets are arranged asymmetrically within the body of the calibration phantom, processing images of the irradiated phantom can identify translations and rotations for positioning the centre of a phantom to coincide with the iso-centre of a treatment apparatus. Having done so, fine adjustments may then be based on the use of a second calibration phantom using containing a single small target positioned in the centre of a calibration phantom thereby improving accuracy.

In accordance with another aspect of the present invention there is provided a method of calibrating a stereoscopic camera system for use with a radio therapy treatment apparatus, the method comprising: positioning a calibration phantom with the phantom's centre at an estimated location for the iso-centre of a radio therapy treatment apparatus; utilizing a stereoscopic camera system to obtain images of the phantom and processing the images to generate a 3D computer model of the surface of the phantom; irradiating the calibration phantom using the radio therapy treatment apparatus and determining the relative location of the centre of the calibration phantom and the iso-centre of the radio therapy treatment apparatus by analysing images of the irradiation of the calibration phantom; and setting the co-ordinate system of the stereoscopic camera system on the basis of the determined relative location of the centre of the calibration phantom and the iso-centre of the radio therapy treatment apparatus and a determined location of the centre of the modelled phantom.

In such an embodiment setting the co-ordinate system of the stereoscopic camera system may comprise: determining the position of the centre of the modelled phantom relative to a current origin for the co-ordinate system for the 3D computer model and adjusting the co-ordinate system for the 3D computer model by the sum of the transformation required to make the current origin for the co-ordinate system for the 3D computer model coincide with the determined position of the centre of the modelled phantom and the transformation required to make location of the centre of the calibration phantom coincident with the iso-centre of the radio therapy treatment apparatus.

The determination of the transformation required to make the current origin for the co-ordinate system for the 3D computer model coincide with the determined position of the centre of the modelled phantom may in some embodiments be determined by storing a 3D computer model of a surface of a calibration phantom with the centre of the calibration model coincident with the centre of the calibration phantom; and determining the transformation required to make the current origin for the co-ordinate system for the 3D computer model coincide with the determined position of the centre of the modelled phantom on the basis of a comparison of the modelled surface of the phantom generated on the basis of images obtained by the stereoscopic camera with the stored model.

The above described systems of calibration have a number of advantages over conventional systems for calibrating stereoscopic camera systems for use with radio therapy apparatus.

Conventionally, the iso-centre of a treatment apparatus is established using an approach such as suggested by Winston Lutz. That location was then normally marked using a laser system so that intersecting planes of laser light coincided at the identified iso-centre and laser light system was then utilised to position a calibration cube for calibrating a stereoscopic camera system. However, the use of the laser light system has the potential to introduce additional errors into the calibration and therefore introduce errors into the accuracy of the patient positioning system. Further the use of a laser light system also requires that the accuracy with which the laser lights identify the iso-centre of a treatment apparatus must be repeatedly checked and confirmed in case this varies over time. Instead in accordance with the claimed invention, the calibration of a stereoscopic camera system is achieved directly through imaging and irradiating a calibration phantom without having to rely upon the positioning of a phantom using lasers. This both increases the accuracy of the calibration and also avoids the need to calibrate the positioning lasers so that they correctly identify the position of the iso-centre over time.

Further details of the present invention will become apparent with reference to the following description and drawings in which:

DETAILED DESCRIPTION OF EXEMPLARY EMBODIMENTS

Figure 1:
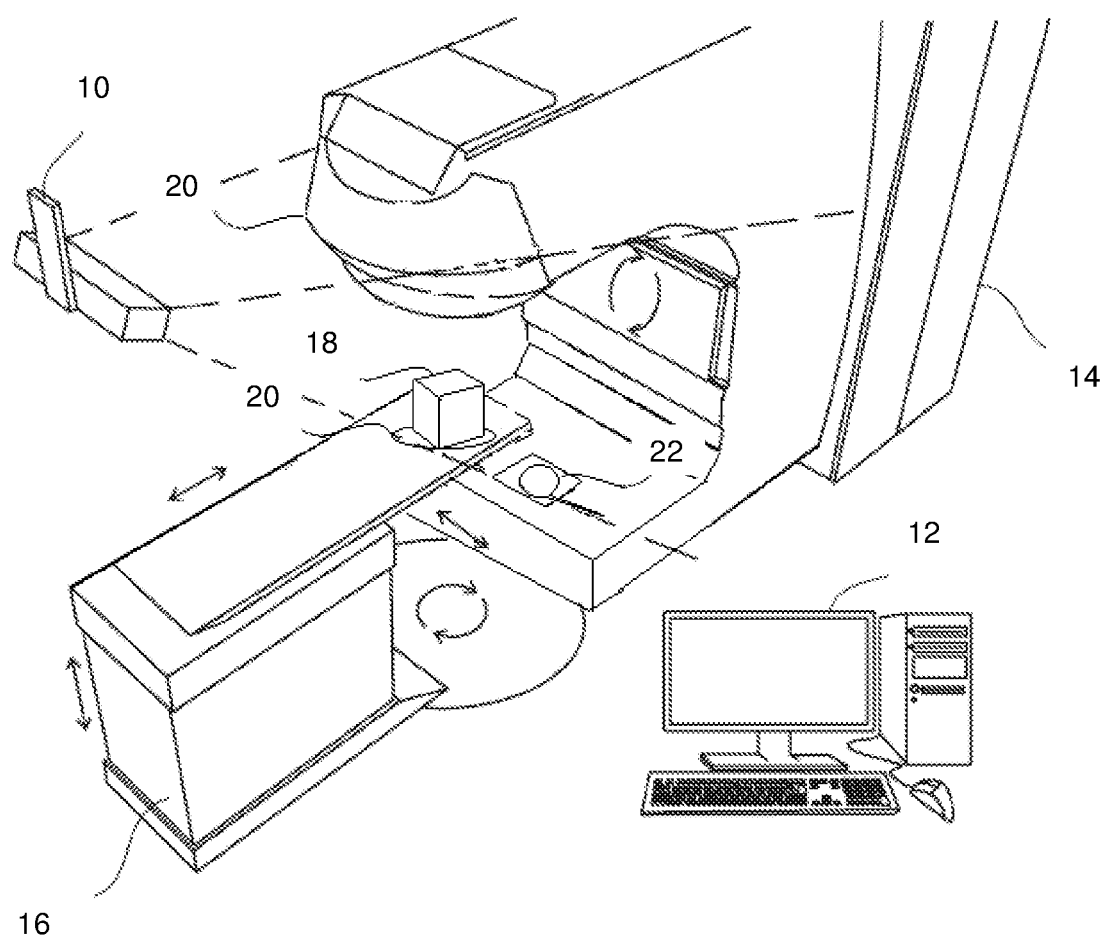
FIG. 1 is a schematic perspective view of a stereoscopic camera system and a treatment apparatus.

FIG. 1 is a schematic perspective view of a treatment system. The treatment system includes a set of stereoscopic cameras 10 that are connected by wiring (not shown) to a computer 12. The computer 12 is also connected to treatment apparatus 14 such as a linear accelerator for applying radiotherapy. A mechanical couch 16 is provided as part of the treatment apparatus. The treatment apparatus 14 and the mechanical couch 16 are arranged such that, under the control of the computer 12, the relative positions of the mechanical couch 16 and the treatment apparatus 14 may be varied, laterally, vertically, longitudinally and rotationally as is indicated in the figure by the arrows adjacent the couch. Additionally, the treatment apparatus 14 is also able to rotate about an axis as indicated by the arrows in the centre of the apparatus in the figure.

The computer 12 is arranged to process images obtained by the stereoscopic cameras 10 to generate 3D wire mesh computer models of the surfaces of objects and people lying on the mechanical couch 16. When appropriately calibrated, a comparison of surface of a patient lying on the couch 16 with a reference surface of the same patient generated during the planning stage of treatment can enable the computer 12 to determine a transformation to match the two surfaces and generate a set of instructions to reposition the mechanical couch 16 so as to minimise differences between the surfaces. When repositioned, the patient can be treated using the treatment apparatus 14 in the knowledge that the patient is in the same position as the position used to determine treatment planning.

In order to minimise errors in the application of radiotherapy and patient positioning it is essential that the stereoscopic camera system 10 and the computer 12 are calibrated to the highest accuracy. In particular, it is necessary that the co-ordinate system used to generate 3D wire mesh models of the surface of a patient is matched both with the iso-centre of the treatment apparatus 14 and the axes of motion of the mechanical couch 16. In most embodiments, the iso-centre of the treatment apparatus 14 will be the location of the zero co-ordinates for the modelling system and the axes of the co-ordinate system for the modelling system will be selected to correspond to the axes of motion (i.e. the lateral, vertical and horizontal axes of motion) of the mechanical couch 16. This then simplifies the conversion of transformations to match model surfaces in model space with instructions for relocating the mechanical couch 16 to match the position of a patient so that they can be treated using the treatment apparatus 14.

Figure 2:
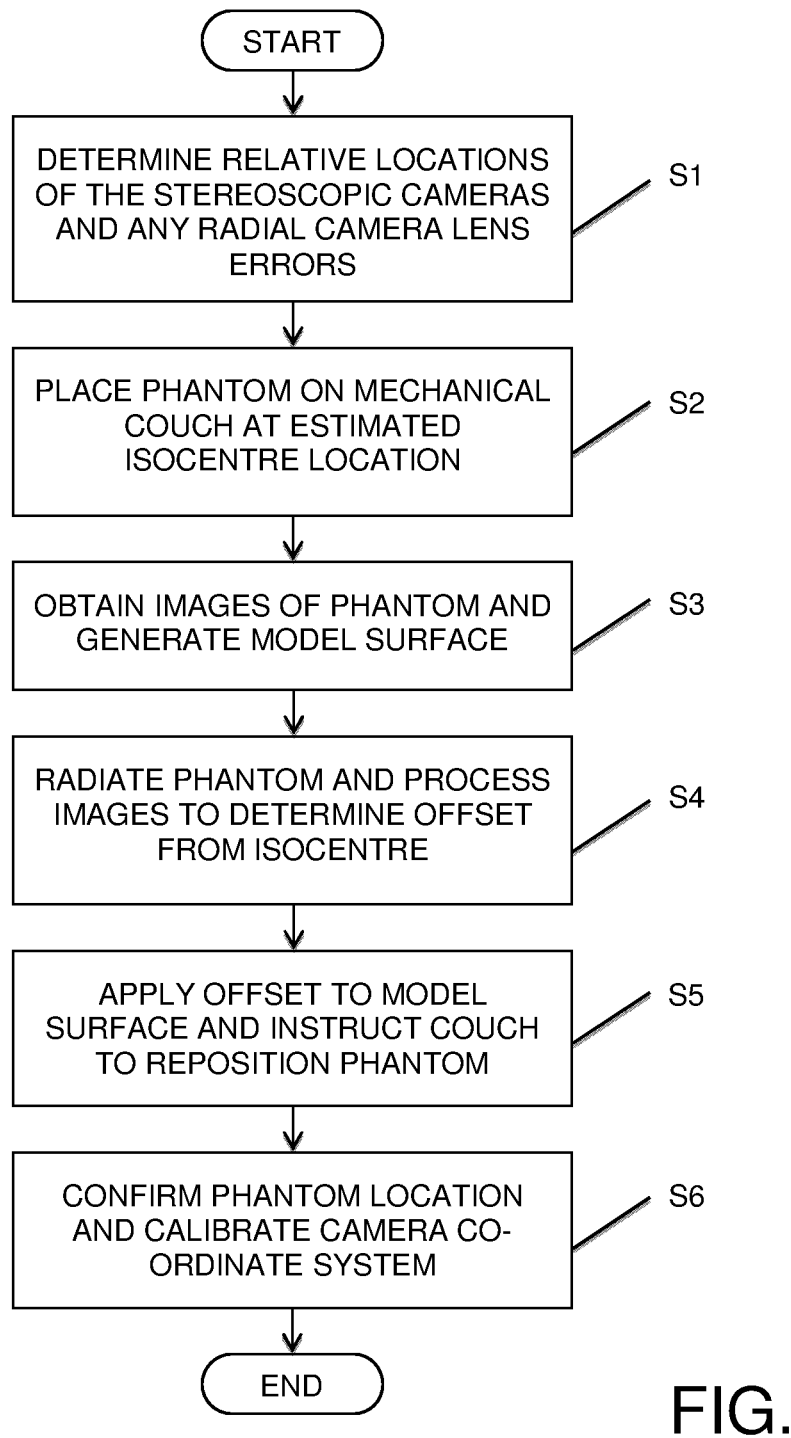
FIG. 2 is a flow diagram of a method of calibration of a stereoscopic camera system in accordance with the present invention.

FIG. 2 is a flow diagram of a method of calibrating the treatment system of FIG. 1.

To calibrate the system, initially (s1) the relative locations of the stereoscopic cameras in the stereoscopic camera system 10 are determined by imaging a calibration sheet such as is described in U.S. Pat. Nos. 7,348,974 and 7,889,906. That is to say that a flat rigid calibration sheet such as a 70*70 cm sheet of material such as aluminum or steel on which a pattern revealing a 3D matrix of circles at known positions on the surface of the sheet is placed on the mechanical couch and imaged by the stereoscopic cameras 10. On the sheet in addition to the pattern of circles are four smaller markers adjacent to four circles the centres of which together identify the four corners of a square of known size.

The images of the sheet obtained by the cameras are then processed by the computer 12 to identify within the image the positions of the four markers in the images. From the relative positions of circles identified by the markers in the images, for each image a first projective transformation is determined which accounts for the estimated centres of the identified circles defining the corners of a projected distorted square in the image which arises due to the relative orientation of the calibration sheet and the camera obtaining the image.

The calculated transform is then utilised to determine estimated three dimensional co-ordinate centres of each of the circles identified by markers. These calculated co-ordinates then identify an estimated location and orientation for the plane corresponding to the surface of the calibration sheet relative to the position from which an image has been obtained.

Each pixel in the image obtained by the cameras 10 is then processed in turn to determine where within the plane containing the estimated positions of the circle centres, each pixel corresponds. The estimated circle centres are then processed in turn and the pixels in an image corresponding to points lying within a pre-determined distance from each circle centre in the calculated plane are then identified. The grey scale values for each of the pixels in each set are then utilised to determine an improved estimate of the co-ordinates for the circle centres. x and y co-ordinates for the positions of the points in the estimated plane including the surface of the calibration sheet each pixel represents within the set is determined. These calculated x and y co-ordinates are then utilised to estimate an improved estimate of the x,y co-ordinates of the circle centre using the following equations:

$$x = \frac{\sum gx}{\sum g}, y = \frac{\sum gy}{\sum g}$$

where $\Sigma g$ is the sum of all pixel values in the set identified for a particular circle centre, $\Sigma gx$ is the sum of the grey scale pixel values for a pixel multiplied by the x co-ordinates for those pixels and $\Sigma gy$ is the sum of the grey scale pixel values for a pixel multiplied by the y co-ordinates for those pixels, and where the colour of the circle is associated with a high grey scale value and the colour of the background corresponding to the calibration sheet is associate with a low grey scale value.

Co-ordinates for the point within the image corresponding to the new estimated circle centres are then determined from these x,y co-ordinates and these updated estimates of the centres of the marked circles are then utilised to determine a more accurate estimated transformation to account for the location and orientation of the calibration sheet. The above process can then be repeated until an accurate estimate of the actual circle centre positions is made and the true transform required to account for the relative orientation of the calibration sheet is determined.

Using the final determined transform, the expected positions of all of the circles on the sheet appearing in the image are then calculated, the portions of the images in the vicinity of each of the estimated circle centres are then processed individually in the same way as described above. For each of the circles a set of pixels is identified corresponding to points within a pre-set distance to the circle centre and then an improved circle centre co-ordinate is calculated using the grey scale values and co-ordinate values as described above.

When the co-ordinates for all the centres of each of the representations of the circles on the calibration sheet have been calculated for an image, the relative orientation of the different cameras within the stereoscopic camera system 10 can then be calculated from the relative positions of these points in the images and the known relative locations of these circles on the surface of the calibration sheet as is described in detail in "A Versatile Camera Calibration Technique for High-Accuracy 3D Machine Vision Metrology Using Off the Shelf TV Cameras and Lenses", Roger Tsai, IEEE Journal of Robotics and Automation, Vol. Ra-3, No. 4, August 1987. Further from the relative positions of the points in the individual images internal camera parameters such as the focal length and radial distortion within the camera images can also be determined.

Thus by performing this initial calibration step, the computer 12 is provided with data which enables the computer to convert stereoscopic images obtained by the stereoscopic camera system 10 into 3D computer wire mesh models of the surfaces of imaged objects. Further, since the initial calibration is performed relative to a calibration sheet of known dimensions, the computer is also provided with data identifying the relationship between distances in the computer models and real world measurements. However, at this stage there is no means by which the computer 12 can relate such measurements to the position of the iso-centre of the treatment room or the axes of motion of the mechanical couch.

Having determined the relative locations and relevant internal parameters of the cameras of the stereoscopic camera system 10, a calibration phantom 18 is then placed (s2) at the estimated iso-centre for the treatment room. The phantom 18 in this embodiment comprises a machined cube of known dimensions of a low density material with radiographic attenuation comparable to water and a density comparable to that of human tissue. In this embodiment, this is achieved by the phantom 18 being a machined polystyrene cube with the surface finish of the cube painted to provide optimal imagery for imaging by the stereoscopic camera system 10. In other embodiments other materials could be used. However, in any embodiment the materials used should be selected to facilitate imaging using imaging techniques such as kV, stereo x-ray, MV or portal imaging, Cone Beam CT, and conventional axial and helical CT.

A known asymmetrical arrangement of targets is provided in a fixed orientation within the body of the phantom 18. These targets may comprise small metallic or ceramic balls. The balls may be made of steel, titanium or tungsten or may be made of a ceramic material or any other material which provides a good contrast to the material forming the body of the phantom 18 when the phantom is imaged. Most suitable materials will be materials which have good radiation stability which are able to withstand considerable radiation dose before undergoing substantial change where the relative density and radiographic attenuation of the targets provided within the body of the phantom 18 is selected to assist with the subsequent imaging of the phantom 18. It is preferable that any phantom 18 contains an asymmetrical arrangement of targets as the asymmetry of the targets enables the orientation of the phantom 18 to be determined from images of the phantom 18, enabling the orientation of the phantom 18 with respect to the treatment co-ordinate system to be determined or confirmed if already known.

Suitable phantoms 18 with an asymmetric arrangement of imaging targets would include the Penta-Guide phantom (Modus Medical Devices, London Ontario, Canada) which consists of an acrylic cube of 16 cm size with five internal air pockets orientated in a unique pattern.

The phantom 18 is located at an estimated location for the iso-centre by being placed on an adjustable table 20 mounted on the mechanical couch 16. The adjustable table 20 in addition to fixing the location of the phantom 18 on the mechanical couch 16 is arranged to have adjustable feet so that minor adjustments to the orientation of the phantom can be made. This is desirable because the axes of motion of a typical mechanical couch 16 are limited to rotation and lateral, vertical and horizontal motion and hence motion of a mechanical couch 16 can only approximate changes in for example pitch or roll. In some embodiments the adjustable table 20 may include a spirit level which can indicate to a user when the table 20 and hence the phantom 18 is level.

So as not to impact the quality of the radiographic images, from any potential x-ray/photon beam scatter, the adjustable table 20 is constructed from materials with low density/radiographic attenuation. In addition, in this embodiment the table 20 has a clear aperture in the path of the vertical treatment beam, so as not to adversely affect the quality of the radiographic images obtained when the phantom 18 is irradiated.

In some embodiments, the adjustable table 20 may be arranged so that it can only be attached to the mechanical couch 16 at a number of fixed locations and in fixed orientations relative to the surface of the mechanical couch 16 Similarly, the adjustable table 20 may also be arranged so that a phantom 18 may only be placed on the table 20 in one or more fixed orientations. Thus for example the adjustable table 20 may include a recess for receiving the phantom 18 in a particular orientation. The attachment of the adjustable table 20 to the mechanical couch 16 and the fixing of the position and orientation of the phantom 18 relative to the adjustable table 20 assists with fixing the positioning and orientation of the phantom relative to the iso-centre and co-ordinate system for the treatment room. In any event the adjustment table 20 should be constructed so as not to slip or move on the surface of the mechanical couch 16.

In some embodiments, the adjustable table may incorporate a micrometer positioning tool for precisely moving the phantom laterally, longitudinally and vertically. The advantage of such a positioning tool would be that it would be easier to make fine amendments to the position of the phantom using the tool rather than the mechanical couch 16 since the relocation would only involve movement of the phantom and not the entire couch 16.

In some embodiments a phantom which incorporated such a tool might be utilized in place of a separate phantom 18 and adjustable table 20. An example of such a phantom would be the Varian Exact T Look-Bar (MedTec, Orange City, IA, USA) which consists of five markers embedded in a tissue equivalent material which is mountable on a couch via a cam lock mechanism which incorporates a micrometer tool.

Having positioned the phantom 18 with its centre point at the estimated treatment room iso-centre and if necessary levelled the phantom 18 by adjusting the feet of the adjustable table 20, images of the phantom 18 are obtained (s3) using the stereoscopic cameras 10. These images are then processed by the computer 12 using the previously obtained information about the relative locations and internal parameters of the cameras of the stereoscopic camera system 10 to create a 3D computer model of the surface of the phantom 18 in the current 3D model space.

The phantom 18 is then irradiated (s4) using the treatment apparatus 14 from a variety of angles and images of the projected radiation are obtained in a conventional manner in a similar way to the conventional Winston-Lutz test using a digital camera 22 arranged at a fixed point opposite the gantry head of the treatment apparatus 14 irradiating the phantom 18. The images obtained by the digital camera 22 when the gantry head of the treatment apparatus 14 is orientated in different locations are then processed by the computer 12 in a conventional way to determine from differences between the appearance of the phantom 18 in the images and in particular shadows of the targets contained within the phantom 18 and compared with the expected locations of shadows of the targets within the phantom on the assumption that the phantom 18 is correctly placed at the iso-centre. From this processing, the computer 12 determines the extent to which the centre of the phantom is offset from the true iso-centre of the treatment apparatus 14.

The computer 12 then (s5) proceeds to apply the determined offset to the modelled surface of the phantom 18 to generate a reference surface for the correct positioning of the phantom 18. Having done so, the computer instructs the mechanical couch 16 to reposition itself laterally, vertically, longitudinally and rotationally so as to relocate the phantom 18 to the position of the true iso-centre. If the phantom 18 is correctly levelled prior to imaging an exact realignment of the phantom 18 should be achievable purely through lateral, vertical, longitudinal and rotational transformations.

As the phantom 18 is repositioned, the location of the phantom 18 is monitored (s6) using the stereoscopic camera system 10 with the computer 12 processing images of the phantom 18 to generate a wire mesh models of the surface of the phantom 18 as it is repositioned. Any differences between the modelled surface and the original surface to which the required offset for relocating the phantom 18 to the true iso-centre can be displayed on the screen of the computer 12 to provide visual feedback of errors which remain.

Monitoring of the motion of the phantom 18 provides an opportunity for confirming that the axes of the co-ordinate system being used to generate wire mesh models corresponds to the axes of the co-ordinate system for the mechanical couch 16. More specifically, the analysis of the images obtained by the digital camera 22 will provide an offset which is the offset for re-positioning the phantom 18 at the true iso-centre for the treatment room. Instructing the mechanical couch 16 to reposition the phantom 18 in a manner corresponding to the offset should result in a motion with corresponds which causes the phantom 18 to be correctly positioned. In addition, the motion of the phantom 18 due to the repositioning of the couch 16 should also correspond to an equivalent relocation of the surface of the phantom 18 as monitored by the stereoscopic camera system 10. Additionally, this monitoring of the surface of the phantom 18 can highlight the existence of any further minor adjustments to the position or orientation of the phantom 18 such as might be achieved by adjusting the adjustable table 20 after the phantom 18 has been repositioned by the mechanical couch 16.

When the phantom 18 located with its centre point at the estimated position of the iso-centre, the stereoscopic camera 10 system can then use the images of the phantom 18 of known dimensions at a known location together with the known relative locations of the cameras of the stereoscopic camera system 10 to calibrate the co-ordinate system for the 3D surface models generated by the computer 12 relative to the actual location of the iso-centre. This is typically achieved by redefining the co-ordinate system for the computer model so that the origin for the computer model co-ordinate system coincides with the centre of the phantom 18 as determined from the modelled surface of the phantom 18 in its new position.

In embodiments of the present invention, steps S3-S6 can be repeated if desired to obtain further confirmation to the relative position of the phantom 18 to the iso-centre. That is to say, after having relocated the mechanical couch 16 based on the determined offset based on images obtained by the digital camera 22 and monitoring that the phantom 18 has been correctly relocated using the stereoscopic camera system 10, the repositioned phantom 18 could then be re-irradiated and further images of the irradiated phantom 18 could then be obtained to confirm that the phantom 18 was indeed located at the iso-centre and if this was not the case further adjustments in the position of the phantom 18 could be made.

For additional accuracy in a second iteration, a phantom 18 could be utilised comprising a single target where the phantom 18 comprises a cube of known dimensions with a single spherical target embedded in the cube where the sphere is located at the centre of the cube. Such a phantom 18 could then be imaged and adjustments made on the basis of analysis of images obtained by the digital camera 22 when the phantom is irradiated. The benefit of such a phantom 18 is that the target sphere could made to be very small and thereby assist with locating the iso-centre with greater accuracy. The disadvantage of such a phantom 18 would be that if only a single target sphere is present, images of the obtained phantom 18 will lack information about the orientation of the phantom 18 which can be derived where the phantom 18 contains an asymmetric arrangement of targets.

A suitable test phantom which consists of one central 2 mm radio-opaque marker embedded in tissue equivalent material would be the Varian cube (Varian Medical Systems, Palo Alto, CA, 15 USA).

In embodiments where multiple phantoms 18 are utilised, it is beneficial that an adjustable table 20 is used which permits attachment of a phantom 18 in a single orientation. In such a system, initially a phantom 18 containing multiple targets could be used to identify the location of the iso-centre of the treatment apparatus. Using the multi-target phantom would have the advantage that because of the asymmetric arrangement of target spheres is apparent, it is possible to determine the orientation of the phantom 18 as it appears in images obtained by the digital camera 22. Having done so and having repositioned the phantom 18 based on analysis of the images, the multi-target phantom 18 could then be replaced with a single target phantom 18 and final minor adjustments could be made to the calibration using the single target phantom. When changing the phantom 18 the stereoscopic camera system 10 could be utilised to ensure that no change in position occurred when the phantoms 18 were exchanged. In such embodiments, it would be beneficial if the multiple phantoms 18 could be marked in a manner (e.g. colour coded) which enabled the individual phantoms 18 to be easily distinguished from one another.

In the above embodiments the calibration of a camera system has been described based upon the imaging of a phantom 18 which has been located to the iso-centre for a treatment room. It will be appreciated that in some embodiments, calibration could be achieved without physically relocating a phantom 18. More specifically, as described, a phantom 18 could be positioned at the estimated location for an iso-centre and imaged using the stereoscopic camera system 18 and then irradiated with images being obtained using the digital camera 22. The images obtained by the digital camera 22 could then be processed to determine the offset of the phantom relative to the actual iso-centre for the treatment room. Similarly, images of the phantom 18 obtained by the stereoscopic camera system 10 could be processed to generate a 3D computer model of the phantom at its current location. An adjustment for the co-ordinate system for the stereoscopic camera 10 could then be calculated by adding the transform calculated by processing the 3D model to relocate the centre of the model of phantom 18 with the origin of the axes for the computer model and the offset as determined by processing the images obtained by the digital camera 22.

The invention claimed is:

1. A radiotherapy system comprising:
a radiotherapy treatment apparatus configured to irradiate a subject positioned relative to a coordinate system of the radiotherapy treatment apparatus;
a stereoscopic camera assembly configured to image the subject, the stereoscopic camera assembly having a camera coordinate system; and
at least one processor configured to process image data obtained by the stereoscopic camera assembly to determine a location of the subject positioned relative to the coordinate system of the radiotherapy treatment apparatus, wherein the at least one processor is configured to calibrate the camera coordinate system by:
receiving image data from the stereoscopic camera assembly of a physical calibration phantom positioned relative to the camera coordinate system;
receiving image data from the radiotherapy apparatus of the irradiated physical calibration phantom; and
using the received image data from the stereoscopic camera assembly of the physical calibration phantom and the received image data from the radiotherapy apparatus of the irradiated physical calibration phantom to determine a difference between the camera coordinate system and the coordinate system of the radiotherapy treatment apparatus.

2. The system according to claim 1, wherein calibrating the camera coordinate system comprises comparing the received image data from the stereoscopic camera assembly of the physical calibration phantom to reference data.

3. The system according to claim 1, wherein calibrating the camera coordinate system comprises comparing the received image data from the radiotherapy apparatus of the physical calibration phantom to reference data.

4. The system according to claim 1, wherein one or more differences between the coordinate system of the stereoscopic camera assembly and the coordinate system of the radiotherapy treatment apparatus is or are used to calculate a transformation between the coordinate system of the stereoscopic camera assembly and the coordinate system of the radiotherapy treatment apparatus.

5. The system according to claim 4, wherein transformation aligns the coordinate system of the stereoscopic camera assembly with the coordinate system of the radiotherapy treatment apparatus.

6. A calibration system for use with a radiotherapy treatment system having a coordinate system, said calibration system comprising:
a stereoscopic camera assembly configured to image a subject positioned relative to a coordinate system of the radiotherapy treatment system, the stereoscopic camera assembly having a camera coordinate system; and
at least one processor configured to calibrate the camera coordinate system relative to the coordinate system of the radiotherapy treatment apparatus, wherein during a calibration:
the stereoscopic camera assembly images a physical calibration phantom positioned relative to the coordinate system of the radiotherapy treatment system;
the at least one processor receives image data of the physical calibration phantom from the stereoscopic camera assembly;
the at least one processor receives radiation image data of the physical calibration phantom irradiated by the radiotherapy treatment system; and
the at least one processor, based at least in part on the received image data of the physical calibration phantom from the stereoscopic camera assembly and the received radiation image data of the irradiated physical calibration phantom, determines a difference between the camera coordinate system and the coordinate system of the radiotherapy treatment apparatus.

7. The system according to claim 6, wherein during a calibration, the at least one processor evaluates the received image data of the physical calibration phantom from the stereoscopic camera assembly with respect to reference data.

8. The system according to claim 7, wherein the at least one processor determines a difference between the camera coordinate system and the coordinate system of the radiotherapy treatment apparatus based at least in part on the evaluation of the received image data of the physical calibration phantom from the stereoscopic camera assembly with respect to reference data.

9. Non-transitory computer readable storage media having data stored therein representing software executable by at least one computer processor for calibrating one or more aspects of a radiotherapy system, the software including instructions stored thereon that when executed on the at least one computer processor, cause the processor to:
receive radiation data of a phantom positioned in a radiotherapy treatment apparatus;
process the radiation data of the phantom to determine at least one of a position or orientation of the phantom, wherein the phantom contains one or more regions of material that provide a differentiated contrast to other regions of the phantom in the irradiation image data representative of the received radiation, and wherein the determination of at least one of a position or orientation of the phantom is based at least in part on the differentiated contrast;
receive image data of an exterior surface of the phantom; and
generate calibration data from information that includes the at least one of the position or orientation of the phantom and the image data of an exterior surface of the phantom.

10. The non-transitory computer readable storage media according to claim 9, wherein the calibration data is generated from information further including reference data.

11. The non-transitory computer readable storage media according to claim 10, wherein the reference data is reference data of the physical calibration phantom.

12. The non-transitory computer readable storage media according to claim 9, wherein the calibration data includes a difference between a coordinate system of a stereoscopic camera assembly used to generate the image data of an exterior surface of the phantom and a coordinate system of a radiation apparatus used to generate the radiation data of a phantom.

13. The non-transitory computer readable storage media according to claim 12, further comprising:
   using one or more differences between the coordinate system of the stereoscopic camera assembly and the coordinate system of the radiation apparatus to calculate a transformation between the coordinate system of the stereoscopic camera assembly and the coordinate system of the radiation apparatus, and wherein the transformation aligns the coordinate system of the stereoscopic camera assembly with the coordinate system of the radiation apparatus.

* * * * *